(12) United States Patent
Bass

(10) Patent No.: US 9,179,947 B2
(45) Date of Patent: Nov. 10, 2015

(54) LOCKING DISTRACTOR WITH TWO-START DISTRACTION SCREW

(75) Inventor: Daniel Bass, Half Moon Bay, CA (US)

(73) Assignee: TEDAN SURGICAL INNOVATIONS, LLC, Sugar Land, TX (US)

(*) Notice: Subject to any disclaimer, the term of this patent is extended or adjusted under 35 U.S.C. 154(b) by 206 days.

(21) Appl. No.: 13/541,223

(22) Filed: Jul. 3, 2012

(65) Prior Publication Data

US 2014/0012269 A1    Jan. 9, 2014

(51) Int. Cl.
| | |
|---|---|
| A61B 17/60 | (2006.01) |
| A61B 17/70 | (2006.01) |
| A61B 17/64 | (2006.01) |
| A61B 17/66 | (2006.01) |
| A61B 17/02 | (2006.01) |
| A61B 17/68 | (2006.01) |
| A61B 17/064 | (2006.01) |

(52) U.S. Cl.
CPC .......... *A61B 17/7077* (2013.01); *A61B 17/025* (2013.01); *A61B 17/64* (2013.01); *A61B 17/6425* (2013.01); *A61B 17/66* (2013.01); *A61B 17/708* (2013.01); *A61B 17/0642* (2013.01); *A61B 2017/0256* (2013.01); *A61B 2017/0648* (2013.01); *A61B 2017/681* (2013.01)

(58) Field of Classification Search
CPC ..................... A61B 17/025; A61B 2017/0256; A61B 17/708; A61B 17/7077; A61B 17/60; A61B 17/64; A61B 17/6425; A61B 17/66; A61B 2017/681
USPC ........................ 606/86 R, 90, 301–318, 105
See application file for complete search history.

(56) References Cited

U.S. PATENT DOCUMENTS

| | | | |
|---|---|---|---|
| 3,709,219 A | 1/1973 | Halloran | |
| 4,957,495 A * | 9/1990 | Kluger | 606/58 |
| 5,219,349 A | 6/1993 | Krag et al. | |
| 6,648,891 B2 | 11/2003 | Kim | |
| 7,494,463 B2 | 2/2009 | Nehls | |
| 7,578,822 B2 | 8/2009 | Rezach et al. | |
| 7,618,424 B2 | 11/2009 | Wilcox et al. | |
| 7,927,337 B2 * | 4/2011 | Keller | 606/90 |
| 7,981,115 B2 | 7/2011 | Justis et al. | |
| 8,172,855 B2 | 5/2012 | Abdou | |
| 8,197,488 B2 | 6/2012 | Sorrenti et al. | |
| 8,394,109 B2 * | 3/2013 | Hutton et al. | 606/105 |
| 8,435,269 B2 * | 5/2013 | Woolley et al. | 606/279 |
| 8,535,320 B2 * | 9/2013 | Woolley et al. | 606/86 A |
| 2004/0210232 A1 * | 10/2004 | Patel et al. | 606/96 |
| 2004/0230191 A1 | 11/2004 | Frey et al. | |

(Continued)

*Primary Examiner* — Larry E Waggle, Jr.
(74) *Attorney, Agent, or Firm* — Kramer Amado, P.C.

(57) ABSTRACT

Various exemplary embodiments relate to a distractor system including one or more of the following: a distraction screw comprising a double threaded distal portion and a non-threaded locking feature near a proximal end of the distraction screw; a crossbar; a first arm coupled to the crossbar; a second arm coupled to the crossbar and having an interior bore sized to receive at least a portion of the distraction screw; and a lock having a nonthreaded aperture sized to receive at least a portion of the distraction screw therethrough, wherein the lock is configurable in a first position and a second position, when configured in the first position the lock engages the locking feature to substantially inhibit axial movement of the distraction screw within the interior bore, and when configured in the second position the lock substantially permits axial movement of the distraction screw within the interior bore.

14 Claims, 16 Drawing Sheets

(56) References Cited

U.S. PATENT DOCUMENTS

| | | |
|---|---|---|
| 2005/0021040 A1 | 1/2005 | Bertagnoli |
| 2005/0203532 A1* | 9/2005 | Ferguson et al. ............... 606/90 |
| 2005/0203533 A1 | 9/2005 | Ferguson et al. |
| 2005/0228388 A1 | 10/2005 | Brodke et al. |
| 2006/0195114 A1 | 8/2006 | Bertagnoli |
| 2006/0247649 A1* | 11/2006 | Rezach et al. ............... 606/90 |
| 2006/0264942 A1 | 11/2006 | Lim et al. |
| 2007/0191856 A1* | 8/2007 | Gil et al. ............... 606/90 |
| 2008/0077155 A1 | 3/2008 | Diederich et al. |
| 2008/0177270 A1* | 7/2008 | Sorrenti et al. ............... 606/90 |
| 2008/0234760 A1* | 9/2008 | Matulaniec ............... 606/309 |
| 2010/0331849 A1* | 12/2010 | Riesinger et al. ............... 606/90 |
| 2011/0130793 A1* | 6/2011 | Woolley et al. ............... 606/279 |
| 2012/0150231 A1 | 6/2012 | Alamin et al. |
| 2013/0172947 A1* | 7/2013 | Greenberg ............... 606/86 A |

* cited by examiner

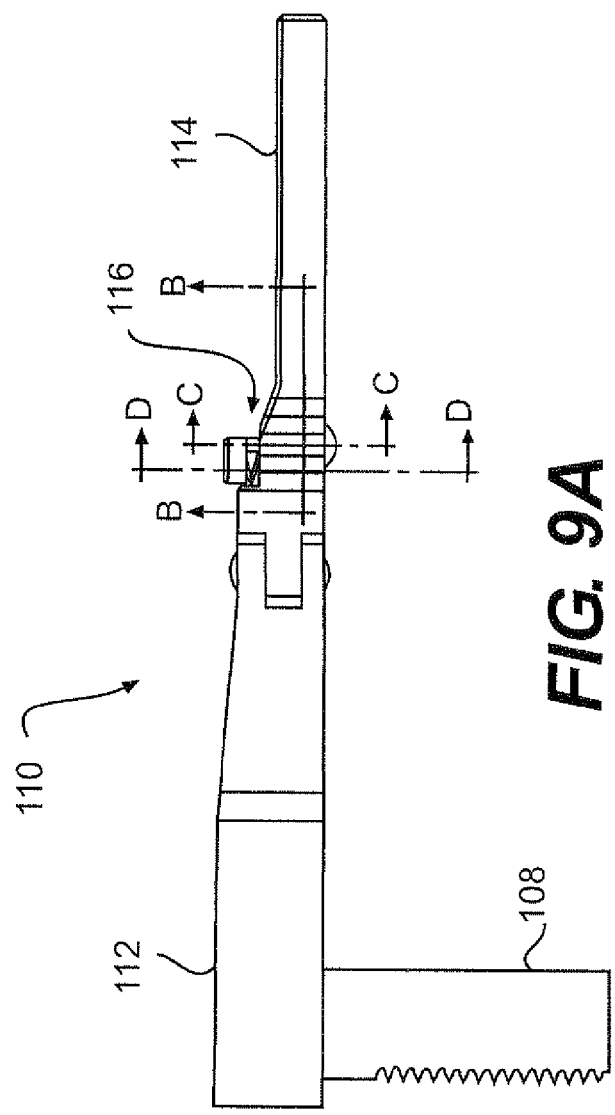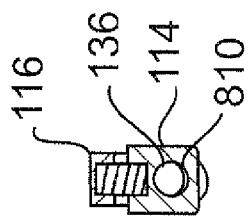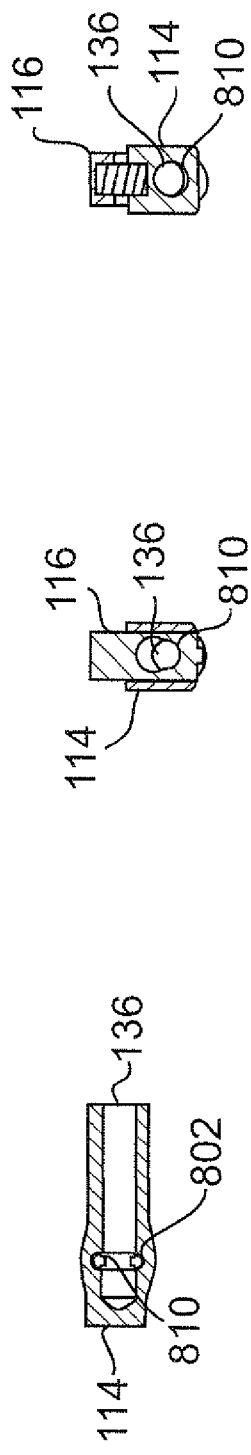

LOCKING DISTRACTOR WITH TWO-START DISTRACTION SCREW

TECHNICAL FIELD

Various exemplary embodiments disclosed herein relate generally to surgical devices.

BACKGROUND

Various surgical procedures involve the distraction of bones away from one another. For example, a spinal discectomy may require that the vertebrae adjacent the disc to be removed be temporarily separated. This separation may enable removal of the disc and subsequent introduction of an intervertebral implant. To effect such distraction, a surgeon may employ the use of a distraction device, specifically adapted to move bones away from one another.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a distractor system including: a distraction screw including a double threaded distal portion and a nonthreaded locking feature near a proximal end of the distraction screw; a crossbar; a first arm coupled to the crossbar; a second arm coupled to the crossbar and having an interior bore sized to receive at least a portion of the distraction screw; and a lock having a nonthreaded aperture sized to receive at least a portion of the distraction screw therethrough, wherein the lock is configurable in a first position and a second position, when configured in the first position the lock engages the locking feature to substantially inhibit axial movement of the distraction screw within the interior bore, and when configured in the second position the lock substantially permits axial movement of the distraction screw within the interior bore.

Various exemplary embodiments relate to a distractor system including: an arm having an interior bore sized to receive at least a portion of a distraction screw; and a lock having a nonthreaded aperture sized to receive at least a portion of the distraction screw therethrough, wherein the lock is configurable in a first position and a second position, when configured in the first position the lock substantially inhibits axial movement of the distraction screw within the interior bore, and when configured in the second position the lock substantially permits axial movement of the distraction screw within the interior bore.

Various exemplary embodiments relate to a distractor system including: a distraction screw including: a distal portion configured to be driven into bone, wherein the distal portion includes a first thread and a second thread that is at least partially intertwined with the first thread, a nonthreaded locking feature near a proximal end of the distraction screw, wherein the nonthreaded locking feature is configured to be engaged by a lock attached to a distractor arm.

Various embodiments are described wherein the second arm includes a proximal arm portion and a distal arm portion movable with respect to the proximal arm portion.

Various embodiments are described wherein the lock is biased into the first position.

Various embodiments are described wherein the lock includes a spring that biases the lock into the first position.

Various embodiments are described wherein: the second arm further includes a slot that extends to the inner bore; and the lock is slideably received within the slot.

Various embodiments are described wherein: the nonthreaded locking feature includes a groove that extends at least part way around the distraction screw; and the nonthreaded aperture of the lock includes a ridge that extends at least part way around an interior surface of the aperture and is sized to fit within the groove of the distraction screw.

Various embodiments are described wherein: the distraction screw further includes an enlarged portion that has a diameter that is greater than a diameter of the interior bore; and the second arm further includes a counterbore at an end of the interior bore, the counterbore sized to receive the enlarged portion.

Various embodiments are described wherein the distraction screw further includes a driver groove that extends at least part way around the distraction screw and is configured to be engaged by a driver tool.

Various embodiments are described wherein: the groove of the nonthreaded locking feature is a square groove; and the driver groove is a round groove.

Various embodiments are described wherein the distractor screw further includes a ribbed portion.

Various embodiments are described wherein the distractor screw further includes: a flange portion; and a hex portion disposed at a proximal end of the flange portion, wherein the flange portion is wider than the hex portion.

BRIEF DESCRIPTION OF THE DRAWINGS

In order to better understand various exemplary embodiments, reference is made to the accompanying drawings, wherein:

FIG. 9A illustrates a top view of an arm of the locking distractor in a closed configuration;

FIG. 9B illustrates a cross section of the arm of the locking distractor in the closed configuration;

FIG. 9C illustrates a cross section of the arm of the locking distractor in the closed configuration;

FIG. 9D illustrates a cross section of the arm of the locking distractor in the closed configuration;

To facilitate understanding, identical reference numerals have been used to designate elements having substantially the same or similar structure or substantially the same or similar function.

DETAILED DESCRIPTION

It will be appreciated that those skilled in the art will be able to devise various arrangements that, although not explicitly described or shown herein, embody the principles of the invention and are included within its scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1:
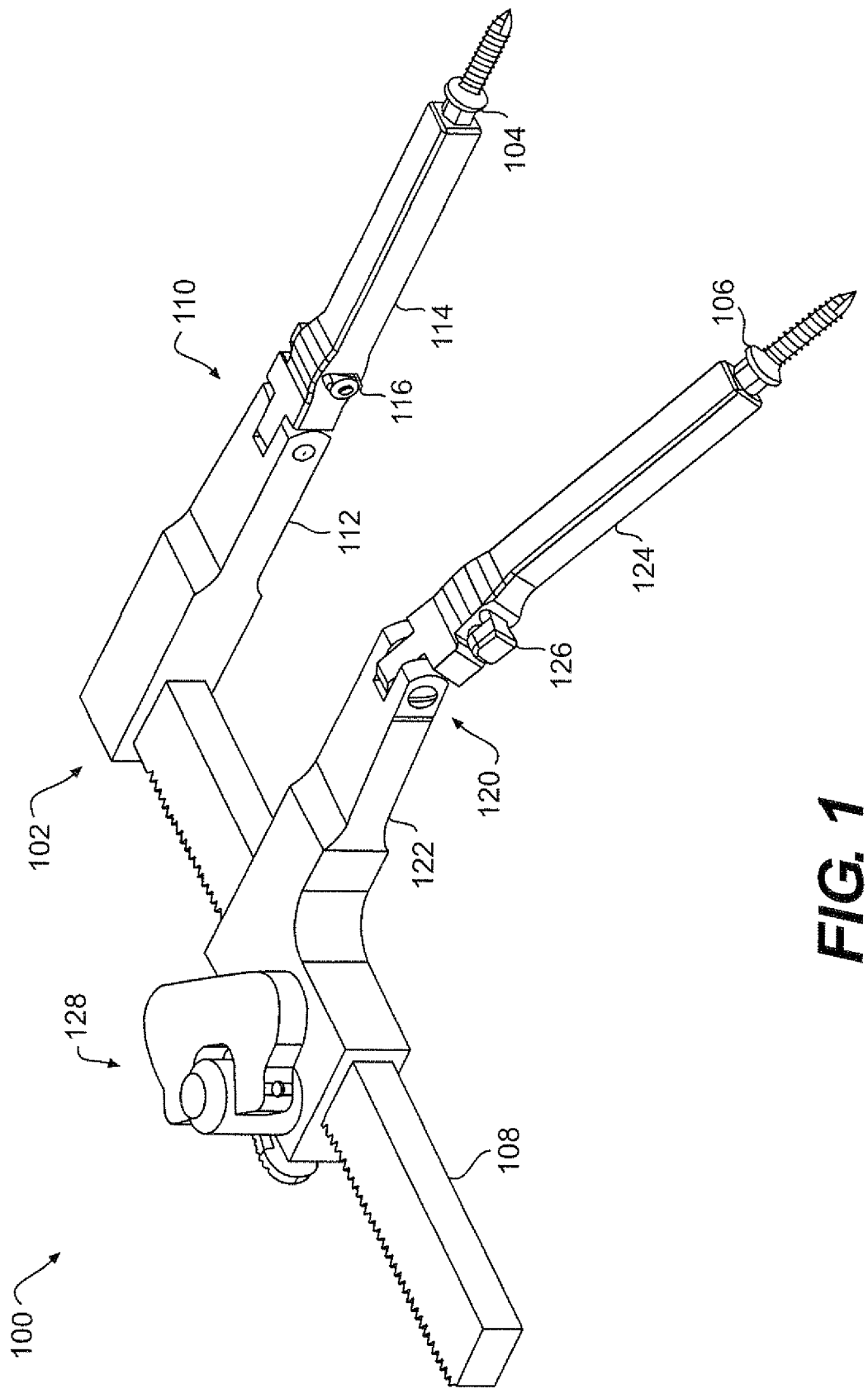
FIG. 1 illustrates a perspective view of an exemplary distractor system.

FIG. 1 illustrates a perspective view of an exemplary distractor system 100. Distractor system 100 may include an exemplary locking distractor 102, a first distraction screw 104, and a second distraction screw 106. Locking distractor 102 may include a crossbar 108, a stationary arm 110, and a locking arm 120. Stationary arm 110 and traveling arm 120 may both constitute distractor arms 110, 120. Stationary arm 110 may include a proximal arm portion 112, a distal arm portion 114, and a lock 116. Traveling arm 120 may include a proximal arm portion 122, a distal arm portion 124, a lock 126, and an adjustment mechanism 128.

Various embodiments herein may be formed from stainless steel. For example, locking distractor 102 may be formed of 17-4 stainless steel, while distraction screws 104, 106 may be formed of 316 stainless steel. It will be understood that various alternative materials may be used to form all or part of distraction system 100.

Stationary arm 110 may be coupled to crossbar 108 such that stationary arm 110 does not move with respect to crossbar 108. For example, proximal arm portion 112 of stationary arm 110 may include a recess sized to receive an end portion of crossbar 108 but not sized to allow the crossbar 108 to advance completely through proximal arm portion 112.

Figure 2:
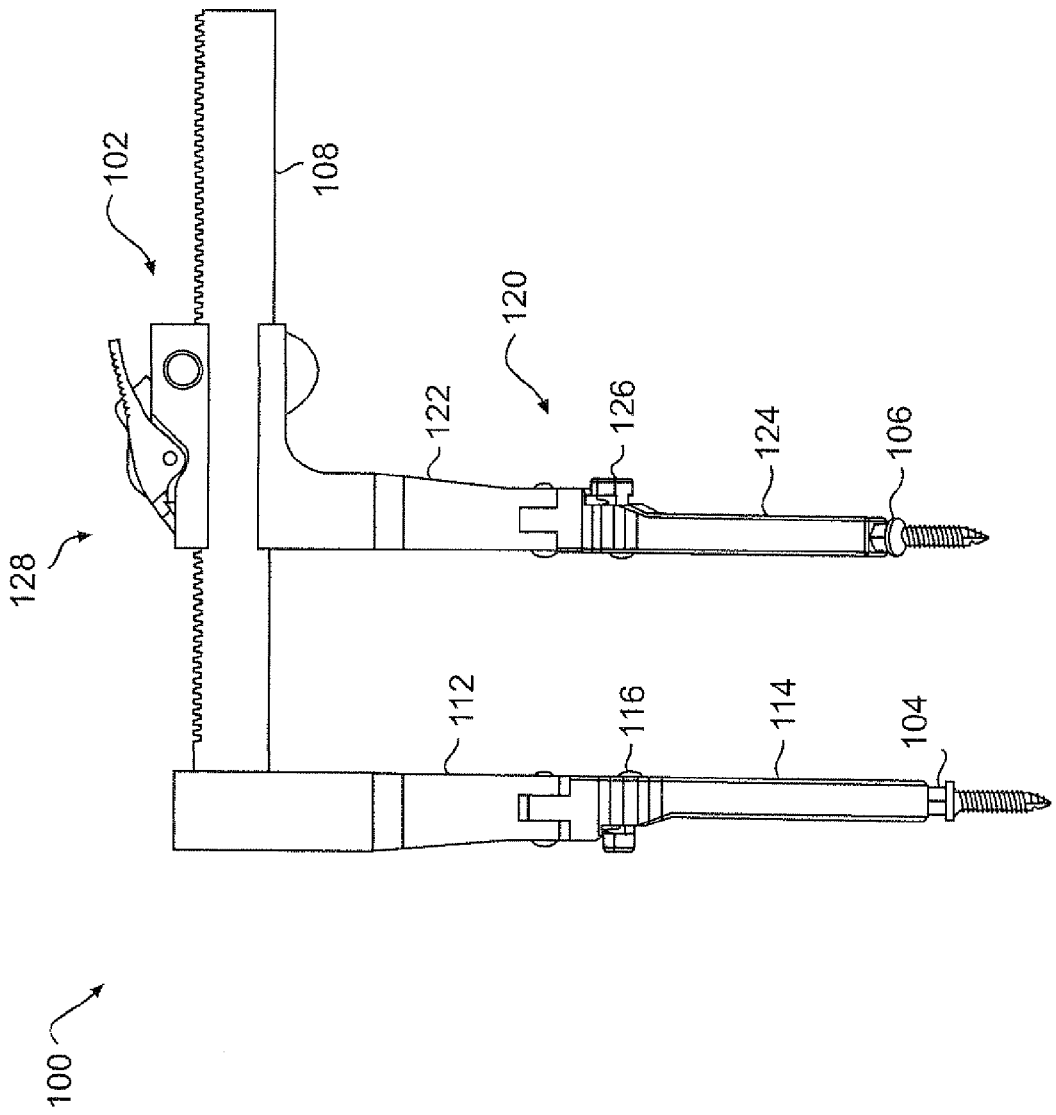
FIG. 2 illustrates a bottom view of the distractor system.

Traveling arm 120 may be coupled to crossbar 108 such that traveling arm 120 is able to move with respect to crossbar 108 and stationary arm 110. As can be seen in FIG. 2, crossbar 108 may pass entirely through proximal arm portion 122 of traveling arm 120. Traveling arm 120 may slide or otherwise move along crossbar 108. As will be explained in greater detail below with respect to FIG. 5, adjustment mechanism 128 may enable locking of the traveling arm 120 to crossbar 108 and fine adjustments of the position of traveling arm 120 along crossbar 108.

Distractor arms 110, 120 may both include multiple portions movably connected to one another. As shown, stationary arm 110 may include proximal arm portion 112 and distal arm portion 114. Distal arm portion 114 may be hingedly attached to proximal arm portion 112 at a connection point, such as a connecting pin, such that distal arm portion 114 may rotate in one or more planes around the connection point. Various alternative structures for connecting proximal arm portion 112 to distal arm portion 114 will be apparent.

As further shown, traveling arm 120 may include proximal arm portion 122 and distal arm portion 124. Distal arm portion 124 may be hingedly attached to proximal arm portion 122 at a connection point, such as a connecting pin, such that distal arm portion 124 may rotate in one or more planes around the connection point. Various alternative structures for connecting proximal arm portion 122 to distal arm portion 124 will be apparent.

Figure 3:
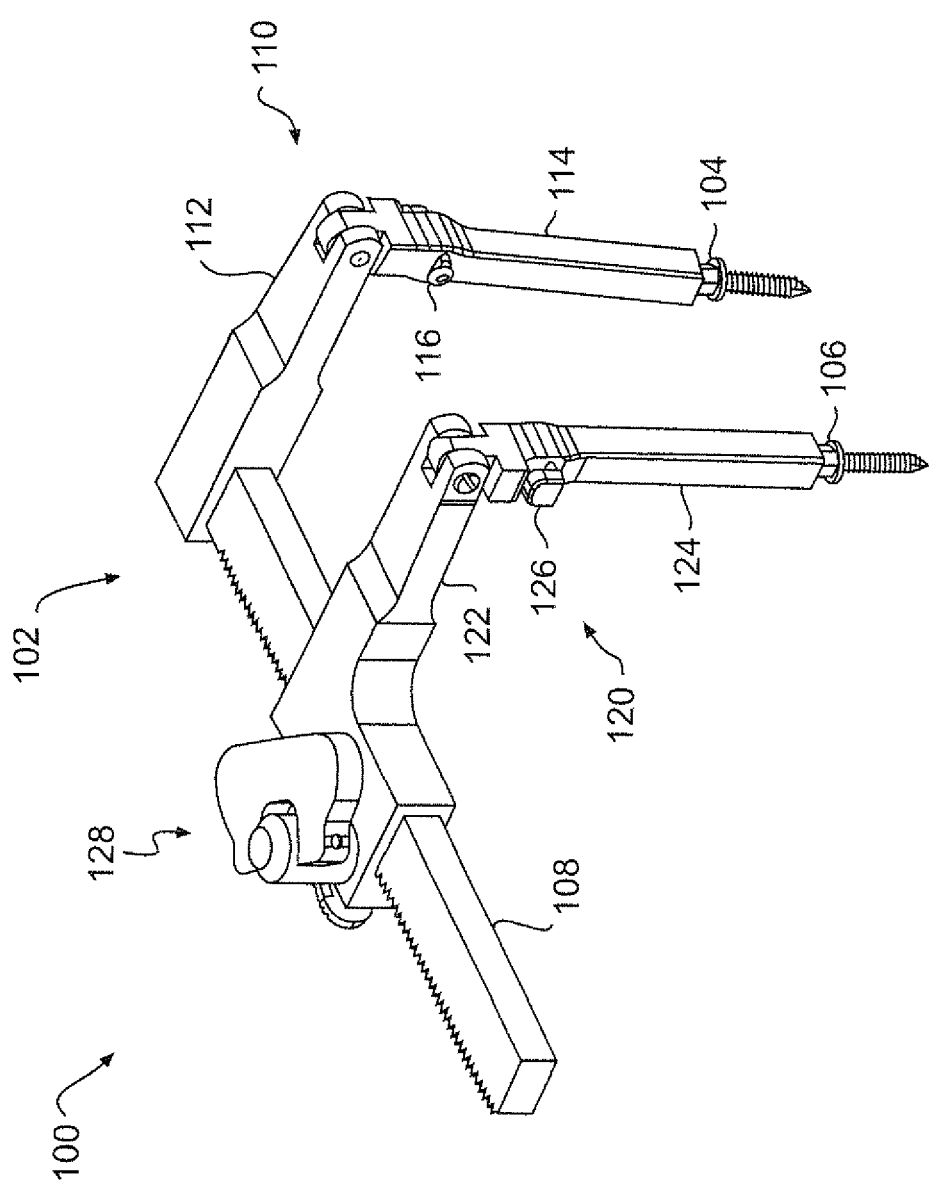
FIG. 3 illustrates a perspective view of the distractor system in an alternate configuration.
Figure 4:
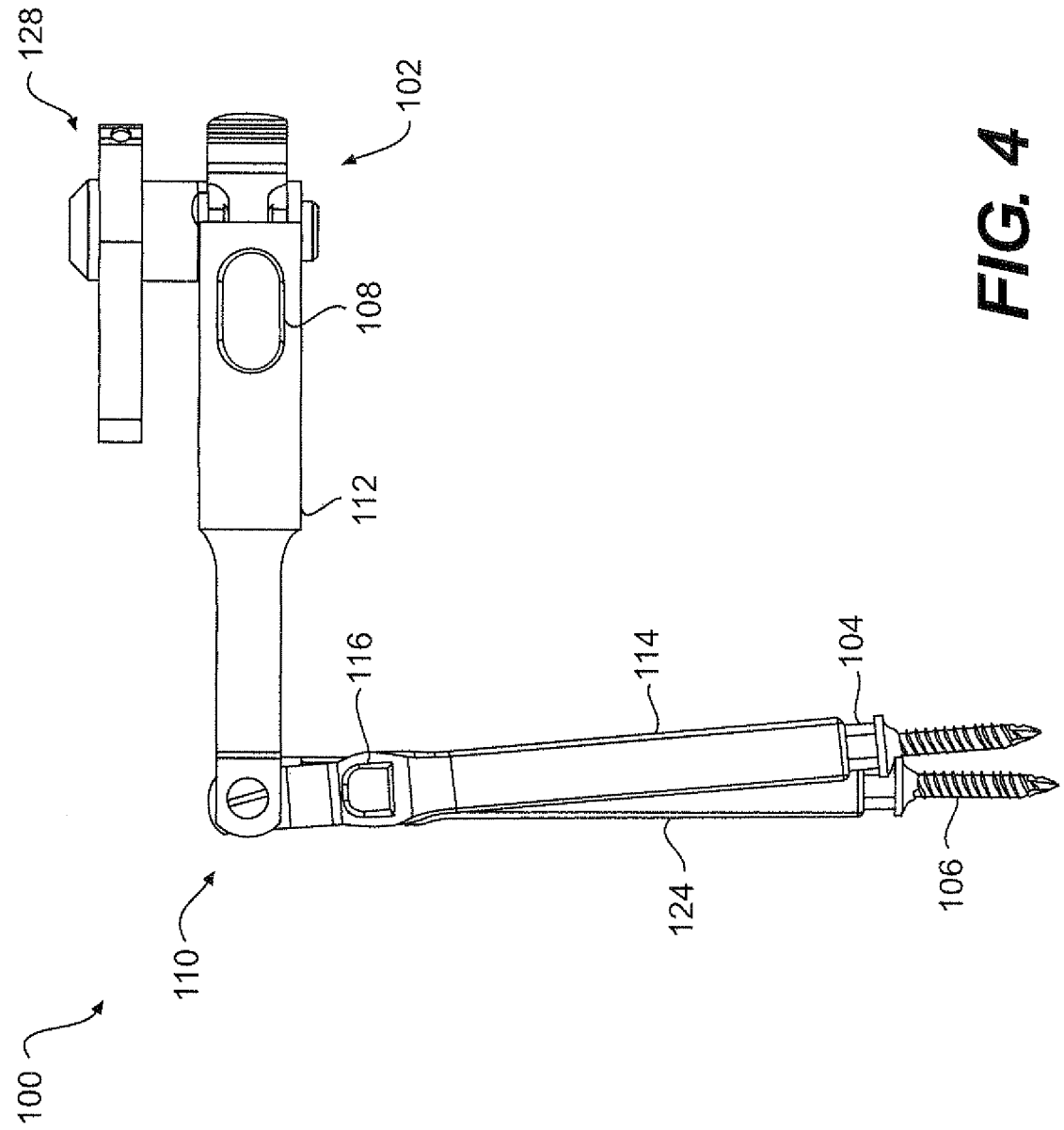
FIG. 4 illustrates a right side view of the distractor system in the alternate configuration.

As described, the distal arm portions 114, 124 may be repositioned to extend in an advantageous direction without repositioning the entire locking distractor 102. For example, as shown in FIGS. 3-4, distal arm portions 114, 124 may be rotated to point generally downward with respect to the remainder of locking distractor 102. Such a configuration may, for example, be advantageous to access the vertebrae of a patent where the locking distractor is mounted above the patient. It will be apparent that various other configurations may be possible. For example, distal arm portions 114, 124 may instead be rotated to point generally upward with respect to the remainder of locking distractor 102. Such a configuration may, for example, be advantageous if the locking distractor 102 were mounted upside down.

As will be explained in greater detail below, distraction screws 104, 106 may be adapted for insertion into bone. Distraction screws 104, 106 may also be sized to be received within distal arm portions 114, 124, respectively. After inserting distraction screws 104, 106 into bone and into distal arm portions 114, 124, a surgeon may operate adjustment mechanism 128 to move distractor arms 110, 120 toward or away from one another, thereby moving the distraction screws 104, 106 and the bones to which distraction screws 104, 106 are anchored.

It will be appreciated that various alternative embodiments may include alternative combinations of stationary and traveling arms. For example, an alternative distractor may include two traveling arms. As another example, a distractor may include two stationary arms coupled to a mechanism that enables the stationary arms to move with respect to one another. It will further be understood that various alternative embodiments may include fewer or additional arms. For example, an alternative embodiment may include three distractor arms or only one distractor arm. Various alternative embodiments may utilize fewer or additional portions for a distractor arm. For example, a distractor arm may include only one portion and no hinges. As another example, a distractor arm may include three portions that are hingedly connected to each other at two positions.

Figure 5:
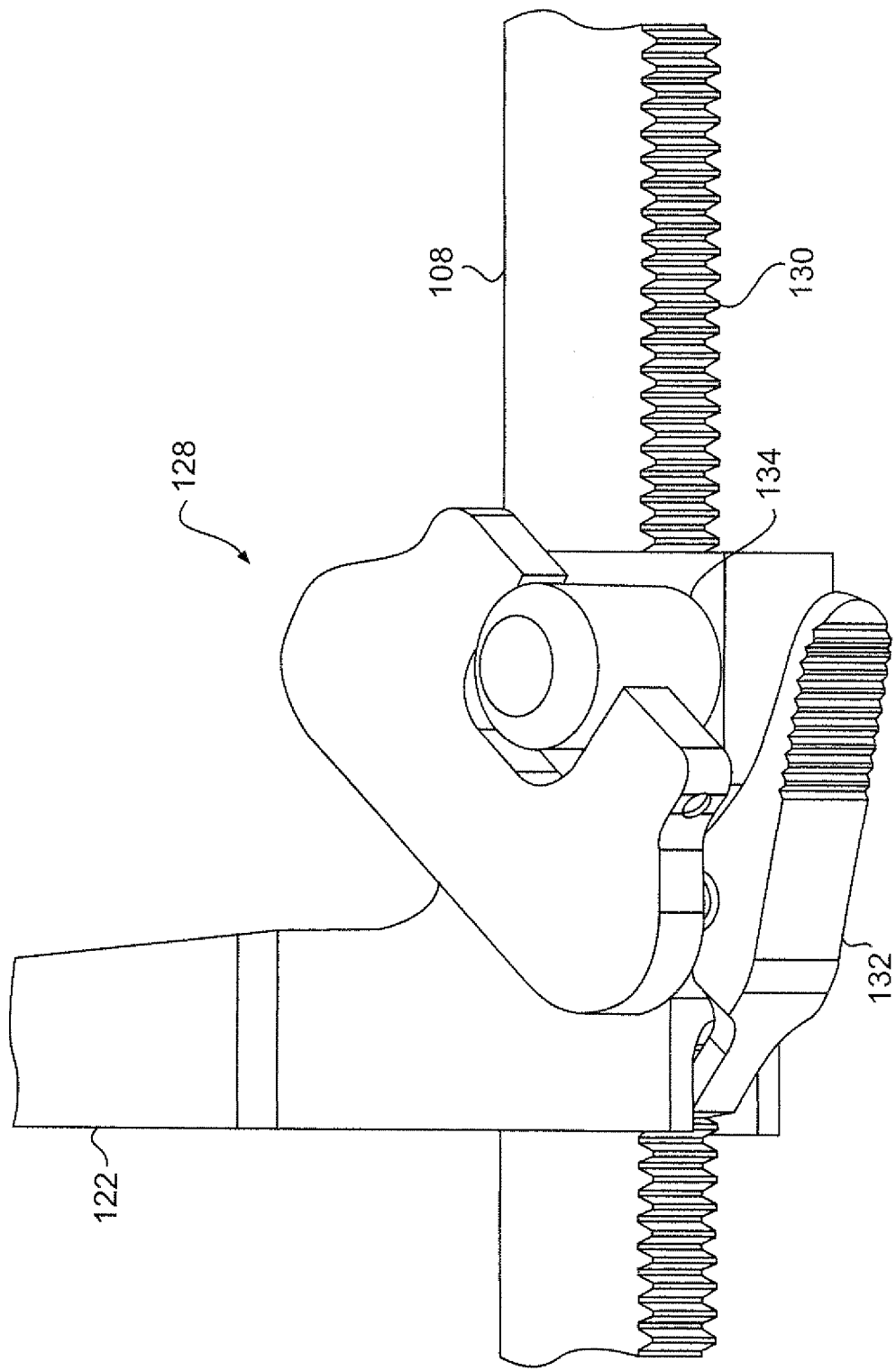
FIG. 5 illustrates a perspective view of an adjustment mechanism of the locking distractor.

FIG. 5 illustrates a perspective view of an adjustment mechanism 128 of the locking distractor 102. As shown, crossbar 108 may include a rack of teeth 130. Connection mechanism may include a ratchet 132 and a pinion 134.

Ratchet 132 may be configured to engage the rack 130 to inhibit movement in one or more directions. Ratchet 132 may include a finger sized to fit between two teeth of rack 130. Ratchet 132 may be pivotally attached to proximal arm portion 122 and biased such that the finger naturally lies against rack 130. In this configuration, ratchet 132 may allow movement of adjustment mechanism 128 along crossbar 108 to the left, as viewed in FIG. 5, and may prevent movement of adjustment mechanism 128 along crossbar 108 to the right, as viewed in FIG. 5. Ratchet 132 may also be manually operable to pivot with respect to proximal arm portion 122, thereby removing the finger from rack 130 and permitting uninhibited motion of connection mechanism 128 along crossbar 108 in either direction.

Pinion 134 may engage rack 130 with mating teeth (not shown). As such, pinion 134 may be manually turned counter clockwise to cause the connection mechanism to travel along crossbar 108 to the right, as viewed in FIG. 5. Pinion 134 may also be manually turned clockwise to cause the connection mechanism to travel along crossbar 108 to the left, as viewed in FIG. 5. Such motion may be impeded, however, if the ratchet is not released and is currently engaged with rack 130.

It will be understood that various alternative adjustment mechanisms may be employed. For example, an alternative adjustment mechanism may include only ratchet 132 or only pinion 134. As another example, an alternative adjustment mechanism may constitute a clamp that may be releasably attached at various points along crossbar 108.

Figure 6:
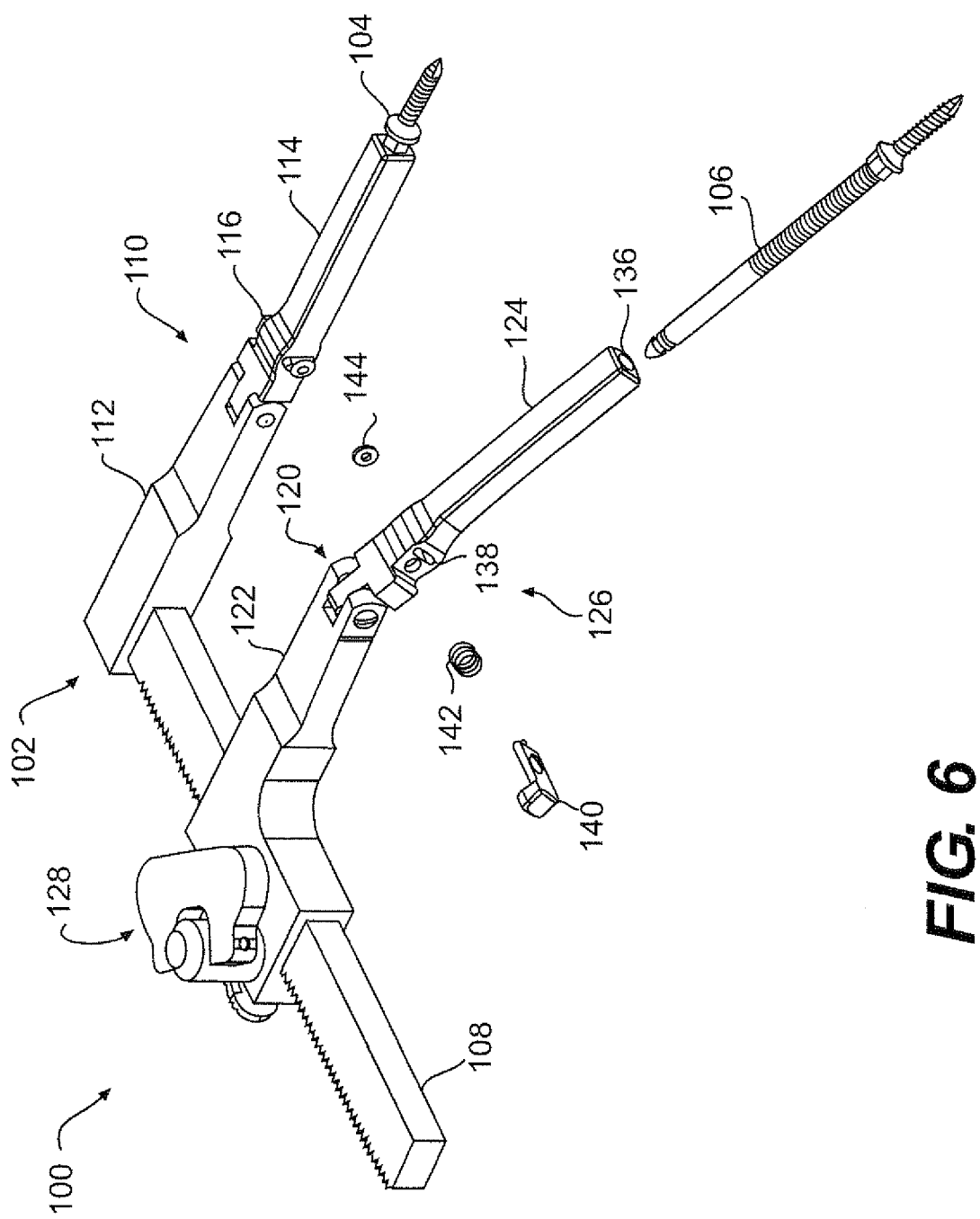
FIG. 6 illustrates a partial exploded view of the distractor system.

FIG. 6 illustrates a partial exploded view of the distractor system 100. As illustrated, distal arm portion 124 may include an interior bore 136 and a slot 138. As further illustrated, lock 126 may include a key 140, spring 142, and cap 144. It will be understood that distal arm portion 114 may include a similar interior bore and slot while lock 116 may include a similar key, spring, and cap.

Interior bore 136 may be sized to receive distraction screw 106. Further, slot 138 may extend from the exterior of distal arm portion 124 to the interior bore 136. In various embodiments, slot 138 may extend from one exterior surface of the distal arm portion 124, through the interior bore 136, to the opposite exterior surface of the distal arm portion. Slot 138 may be sized to receive a portion of key 140 therethrough, such that key 140 may be partially disposed within interior bore 136.

As will be described in greater detail below, key 140 may be slidable within slot 138 between an open and a closed position. Spring 142 may be a compression spring and may bias key 140 in the closed position. Cap 144 may attach to the key 140 to prevent spring 142 from ejecting key 140 from slot 138.

Figure 7:
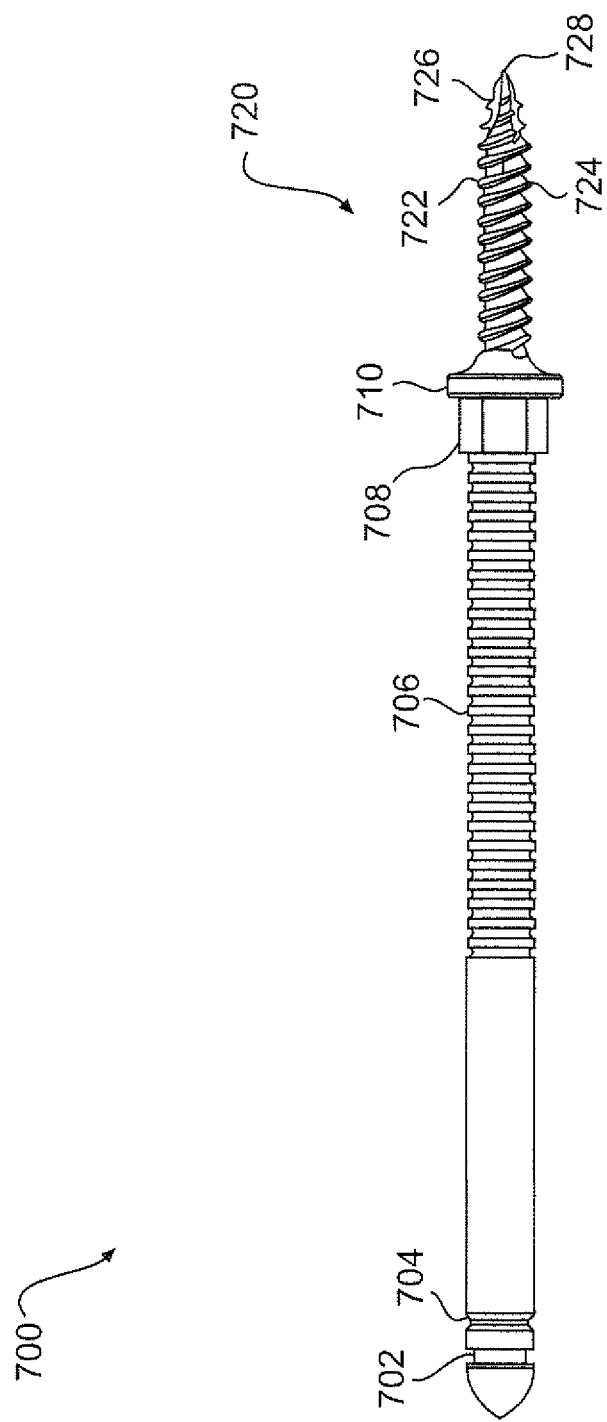
FIG. 7 illustrates a top view of an exemplary distraction screw.

FIG. 7 illustrates a top view of an exemplary distraction screw 700. It will be understood that distraction screw 700 may correspond to either distraction screw 104 or distraction screw 106. Distraction screw 700 may include a locking feature 702, driver groove 704, ribbed portion 706, hex portion 708, flange portion 710, and threaded portion 720.

Locking feature 702 may be a feature configured to be engaged by a lock. As illustrated, locking feature 702 may include a groove having a substantially square profile. This square groove may be sized to receive a ridge of a lock, as will be described in greater detail below. Driver groove 704 may be a feature configured to enable a driver tool (not shown) to engage distraction screw 700. Driver groove may have a substantially round profile. A driver tool (not shown) may include a round ridge or ring that, when coupled to distraction screw 700, engages with driver groove 704 to retain the screw 700 within the driver.

Ribbed portion 706 may include one or more grooves that provide the body of screw 700 with a plurality of ribs. For example, as shown, ribbed portion 706 may include twenty-six evenly-spaced circular grooves. In various alternative embodiments, ribbed portion 706 may include one or more threads or helical grooves that provide ribs. Ribbed portion 706 may provide additional friction to resist screw 700 falling out of a distractor such as locking distractor 102 or another distractor (not shown) that may or may not include locking features.

Hex portion 708 may be wider than other portions of distraction screw 700 and may include six faces. Hex portion may be adapted for engagement with an end of a driver tool (not shown), such that the driver tool may rotate distraction screw 700, such that distraction screw may be driven into bone. Various alternative configurations for hex portion 708 will be apparent. For example, hex portion 708 may include fewer or additional faces. For example, hex portion 708 may have 10 sides or may be star shaped.

Flange portion 710 may be wider than other portions of distraction screw 700. For example, as shown, flange portion 710 may be the widest portion of distraction screw 700. Flange portion 710 may provide a stop to indicate when screw 700 has been sufficiently driven into bone and should not be driven further. Additionally, flange portion 710 may provide a surface on which a driver tool (not shown) may rest as the tool acts on hex portion 708.

Threaded portion 720 may include threads 722, 724, one or more flutes 726, and a pointed tip 728. Flutes 726 and pointed tip 728 may enable screw 700 to begin driving and cutting threads into bone. Threaded portion 720 may be double threaded to increase the rate at which screw 700 is driven into bone per turn. As such, threaded portion 720 may include a first thread 722 and a second thread 724. Threads 722, 724 may be intertwined with each other to provide for screw 700 to be driven into bone faster and more efficiently. For example, threads 722, 724 may have a thread pitch of 1 mm, thereby providing for advancement of the screw 700 by 2 mm per turn.

Figure 8:
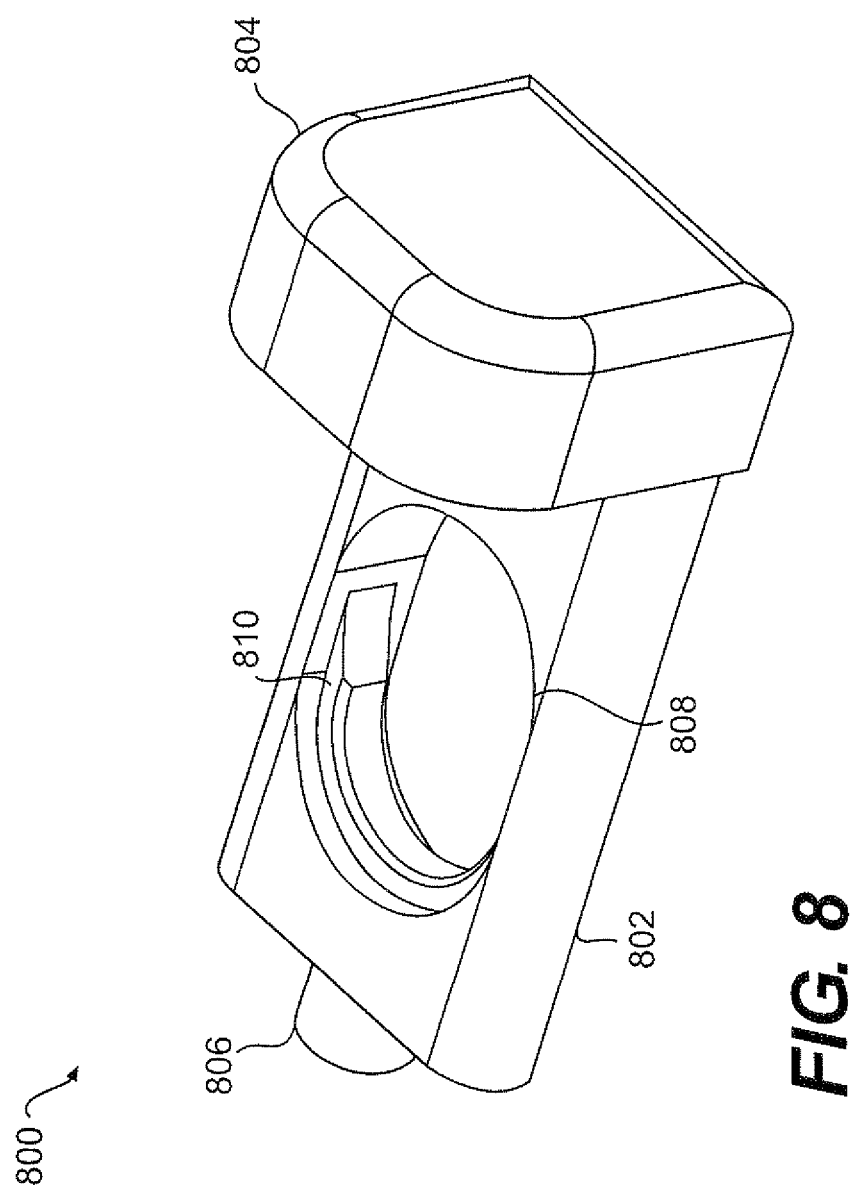
FIG. 8 illustrates a perspective view of a key.

FIG. 8 illustrates a perspective view of a key 800. Key 800 may correspond to key 140 of lock 126 or to a key of lock 116. Key 800 may include body 802, button 804, and peg 806. Body 802 may be shaped and sized to be slideably received within a slot of a distal arm portion, such as slot 138 of distal arm portion 124. Body portion may include an aperture 808 formed therein. Aperture 808 may be large enough to allow at least a portion of a distraction screw, such as screw 700, to pass therethrough. Aperture 808 may also include a ridge 810 disposed at least part way around the interior of aperture 808. Ridge 810 may be substantially square or may otherwise be shaped to be received within a locking feature of a distraction screw. For example, ridge 810 of key 800 may be received within locking feature 702 of distraction screw 700. It will be appreciated that alternative engagements may be used. For example, aperture 808 may instead include a groove (not shown) which may receive a ridge locking feature (not shown) of a distraction screw.

Button 804 may be an enlarged portion that is sized to not fit within a slot such as slot 138. Button 804 may be sized and shaped to be manually pushed in to advance body through a slot such as slot 138. Peg 806 may be sized and shaped to extend out of a slot and be inserted through a cap (not shown) such as cap 144. Such cap (not shown) may retain key 800 within the slot so that a spring (not shown) does not force the key 800 back out of the slot.

FIG. 9A illustrates a top view of an arm 110 of the locking distractor 102 in a closed configuration. As shown, lock 116 is not depressed and is biased outward, into the closed position. FIG. 9B shows a partial cross-sectional view taken along line B-B. As shown, in the closed configuration, ridge 810 of lock 116 is disposed in line with inner bore 136. FIG. 9C shows a partial cross-sectional view taken along line C-C, while FIG. 9D shows a partial cross-sectional view taken along line D-D. As further shown in FIGS. 9C-D, when in the closed configuration, ridge 810 of lock 116 is disposed in line with inner bore 136. Thus, when lock 116 is not being acted upon by an external force, lock 116 rests in the closed configuration and ridge 810 may be disposed in line with inner bore 136.

Figure 10A:
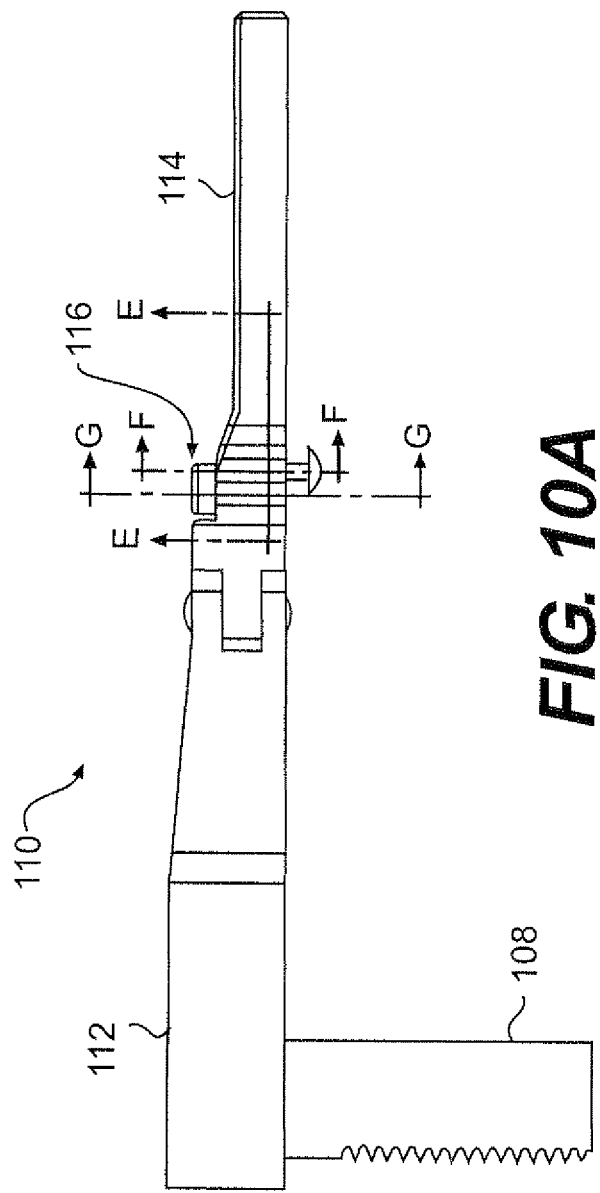
FIG. 10A illustrates a top view of an arm of the locking distractor in an open configuration.
Figure 10C:
FIG. 10C illustrates a cross section of the arm of the locking distractor in the open configuration.
Figure 10D:
FIG. 10D illustrates a cross section of the arm of the locking distractor in the open configuration.
Figure 10B:
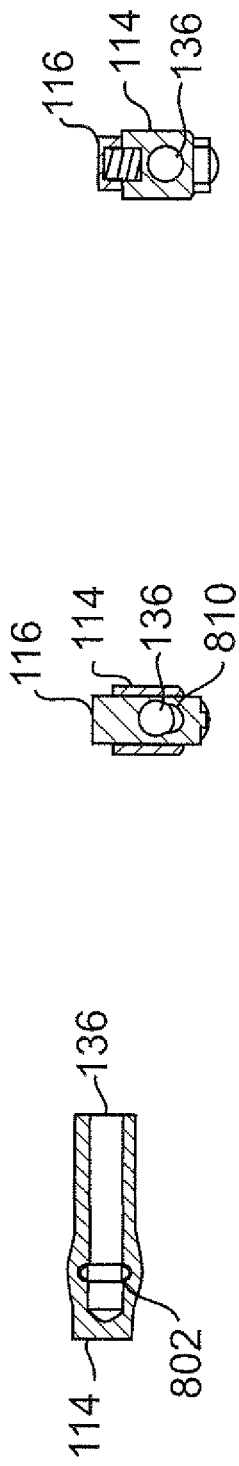
FIG. 10B illustrates a cross section of the arm of the locking distractor in the open configuration.

FIG. 10A illustrates a top view of an arm 110 of the locking distractor 102 in a closed configuration. As shown, lock 116 is depressed to overcome the biasing force and take on the open position. FIG. 10B shows a partial cross-sectional view taken along line E-E. As shown, in the open configuration, ridge 810 of lock 116 is not disposed in line with inner bore 136. FIG. 9C shows a partial cross-sectional view taken along line C-C, while FIG. 9D shows a partial cross-sectional view taken along line D-D. As further shown in FIGS. 9C-D, when in the open configuration, ridge 810 of lock 116 pushed out of line with inner bore. Thus, when lock 116 is depressed, lock 116 is disposed in the open configuration and ridge 810 may not be disposed in line with inner bore 136. As such, a distraction screw (not shown) may be free to slide through the aperture of lock 116 and therefore may slide freely within interior bore 136.

It will be noted that the foregoing description with respect to stationary arm 110 may also be applicable to traveling arm 120. For example, the lock 126 of traveling arm 120 may operate in a substantially similar manner to that described above with respect to lock 116.

Figure 11:
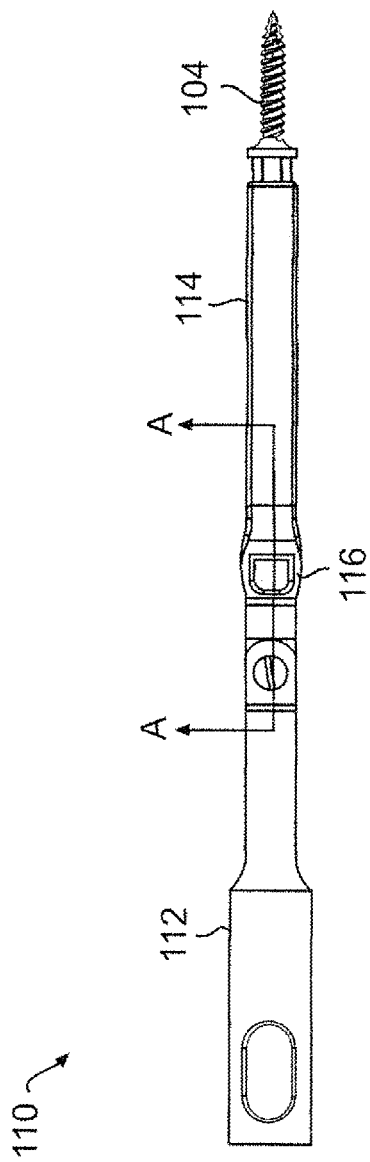
FIG. 11 illustrates a right side view of an arm of the locking distractor and a distraction screw.
Figure 12:
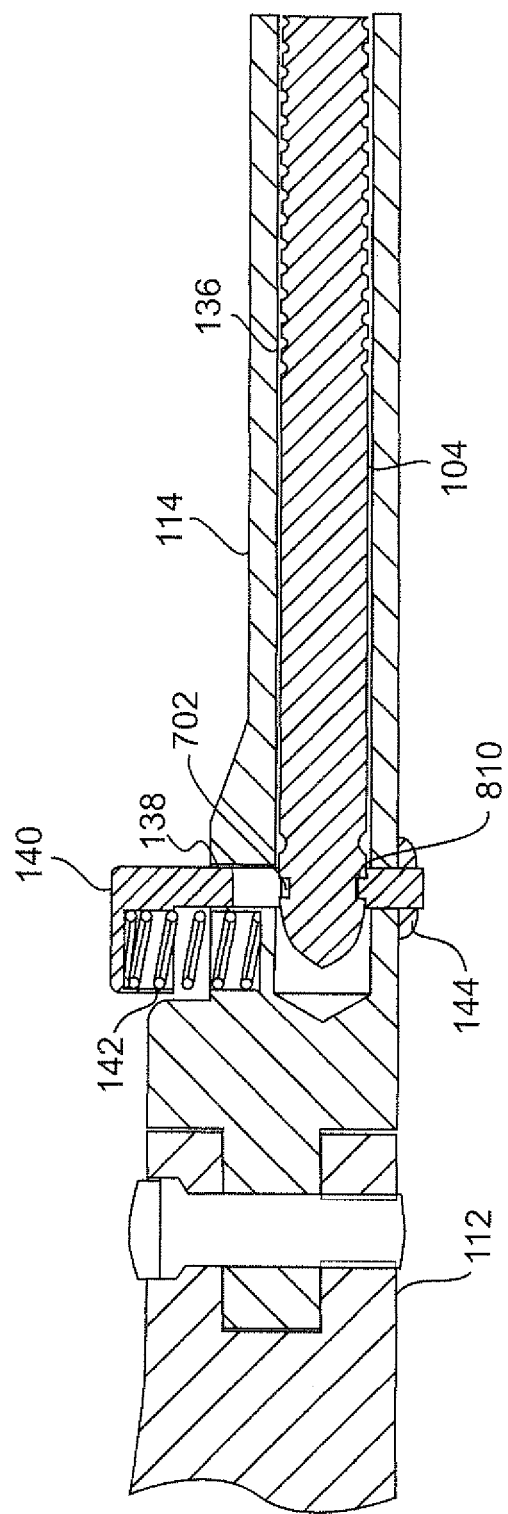
FIG. 12 illustrates a cross section of the arm of the locking distractor and the distraction screw in a closed position.

FIG. 11 illustrates a right side view of an arm 110 of the locking distractor 102 and a distraction screw 104. As shown, distraction screw may be received within distal arm portion 114. Lock 116 may currently be situated in either the closed position or the open position. FIG. 12 may illustrate a partial cross section view taken along line A-A when lock 116 is in the closed position. As illustrated, spring 142 may bias key 140 upward, as view in FIG. 12, while cap 144 may prevent key from leaving slot 138. In this closed configuration, ridge 810 of body 140 may engage with locking feature 702 of distraction screw 104. This engagement may substantially inhibit screw 104 from sliding within interior bore 136, thereby locking distraction screw 104 in place.

Figure 13:
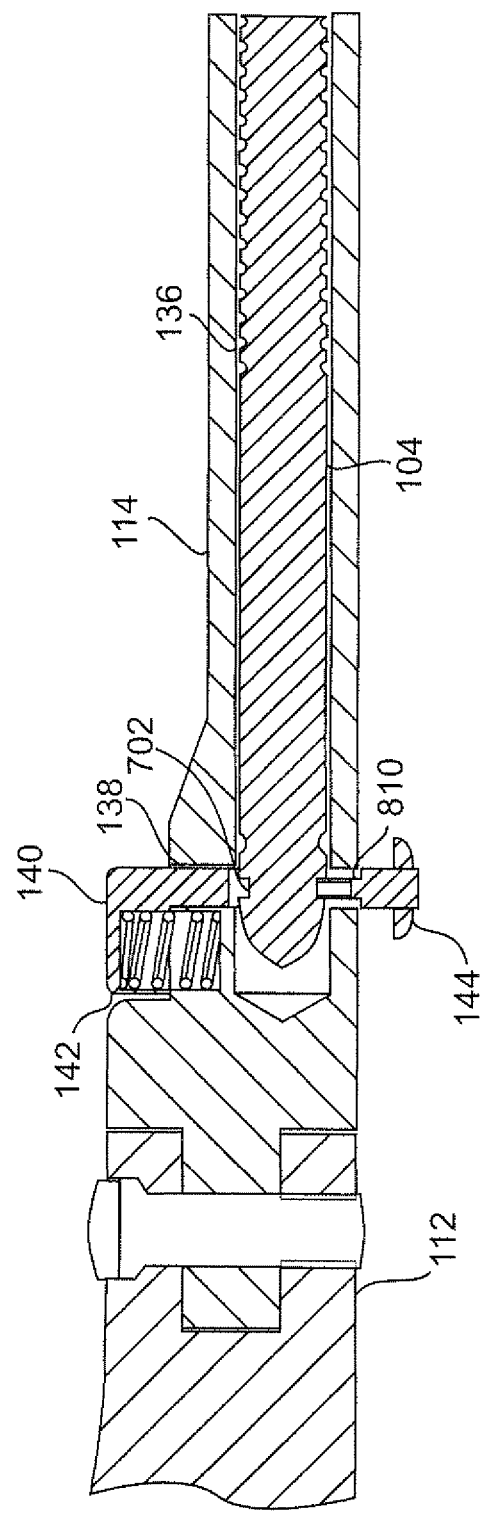
FIG. 13 illustrates a cross section of the arm of the locking distractor and the distraction screw in an open position.

FIG. 13 may illustrate a partial cross section view taken along line A-A when lock 116 is in the open position. As illustrated, when a force is applied to body 140 to overcome the biasing force of spring 142, body 140 may slide through slot 138 to occupy the open position. This sliding may move ridge 810 out of interior bore 136 or out of engagement with locking feature 702. Thus, when body 140 occupies the open position, screw 104 may freely move within interior bore 136.

Figure 14:
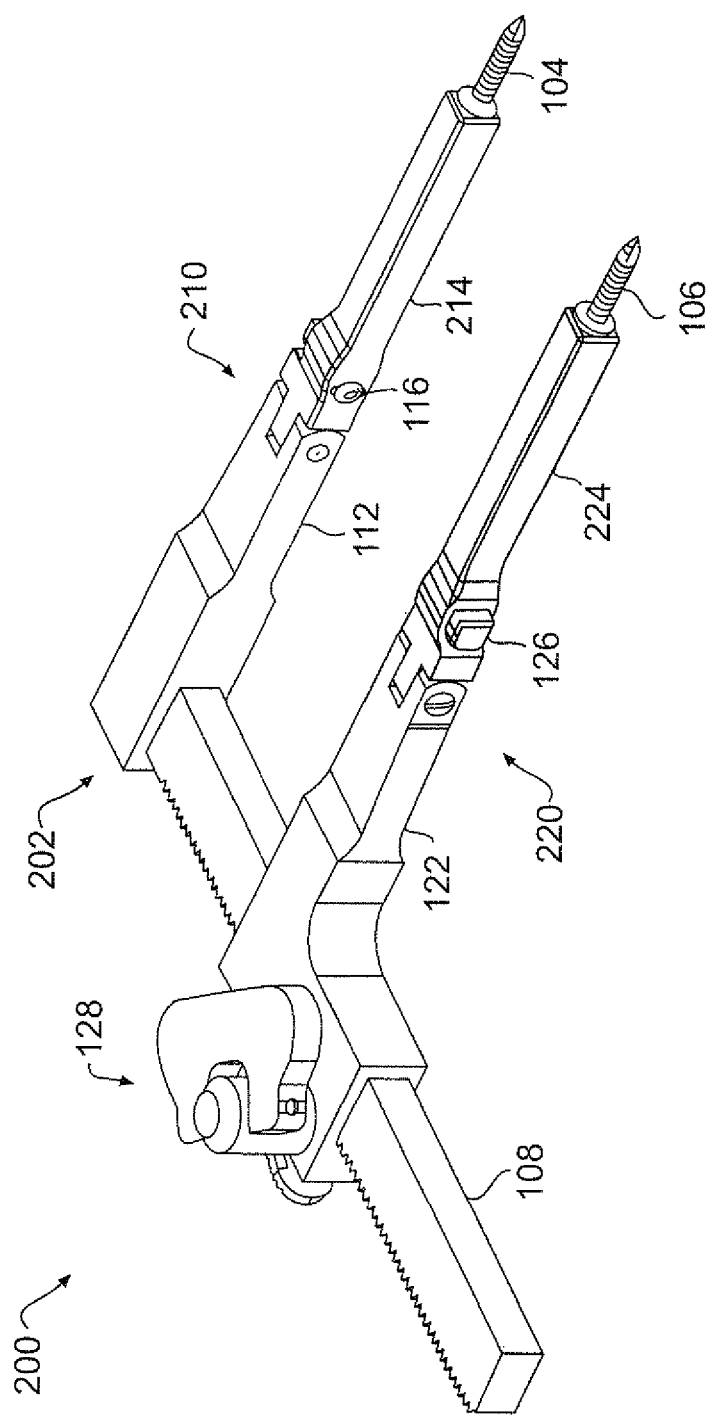
FIG. 14 illustrates a perspective view of an alternative embodiment of a distractor system.
Figure 15:
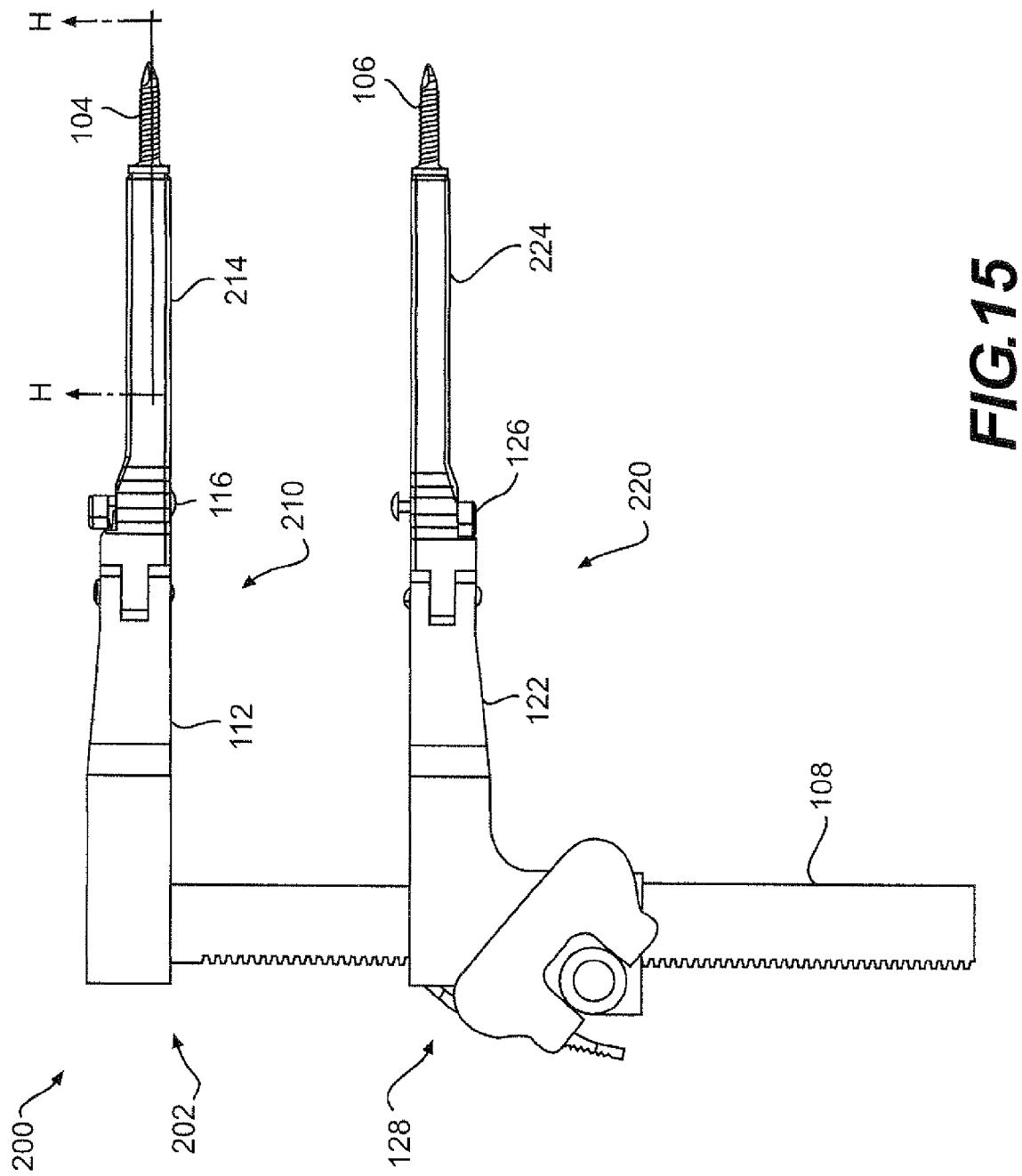
FIG. 15 illustrates a top view of the alternative embodiment of the distractor system.

FIG. 14 illustrates a perspective view of an alternative embodiment of a distractor system 200. FIG. 15 may illustrate a top view of the alternative embodiment of a distractor system 200. Distractor system 200 may include an exemplary locking distractor 202, a first distraction screw 104, and a second distraction screw 106. Locking distractor 202 may include a crossbar 108, a stationary arm 210, and a locking arm 220. Stationary arm 210 and traveling arm 220 may both constitute distractor arms 210, 220. Stationary arm 210 may include a proximal arm portion 112, a distal arm portion 214, and a lock 116. Traveling arm 120 may include a proximal arm portion 122, a distal arm portion 224, a lock 126, and an adjustment mechanism 128.

Distractor system 200 may differ from distractor system 100 in that distal arm portions 214, 224 may be sized and configured to receive more of screws 104, 106 than distal arm portions 114, 124. For example, as shown in FIG. 1, the hex portions of screws 104, 106 may be disposed outside of distal arm portions 114, 124. Returning to FIGS. 14-15, the hex portions of screws 104, 106 may be disposed inside distal arms portions 214, 224.

Figure 16:
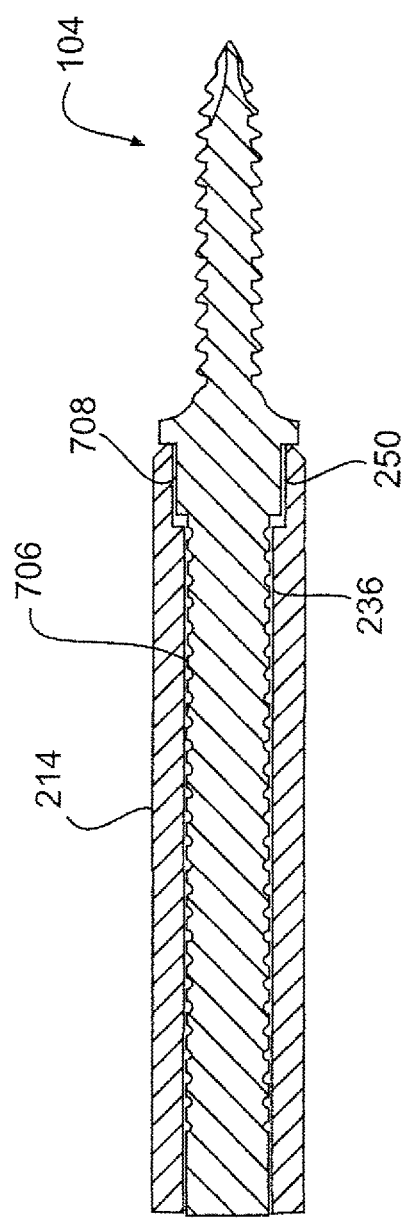
FIG. 16 illustrates cross section of a distraction screw and an arm of the alternative embodiment of a locking distractor.

FIG. 16 may illustrate a partial cross section view taken along line H-H. As shown, distal arm portion 214 may include an interior bore 236 and a counterbore 250. It will be understood that distal arm portion 224 may include a similar bore and counterbore (not shown). Interior bore 236 may be sized to receive portions of the distraction screw 104, such as ribbed portion 706, but may not be sized to receive other portions of the distraction screw 104, such as hex portion 708. Counterbore 250 may begin at the distal end of distal arm portion 214 and may be sized to receive at least some of hex portion 708. As such, hex portion 708 of screw 104 may be recessed within distal arm portion 214 during use.

According to the foregoing, various exemplary embodiments enable a distractor that provides a more secure engagement with distraction screws. By providing a biased locking mechanism, a distractor may lock an engagement screw in place within a distractor arm during the performance of a distraction procedure. Further, by providing a distraction screw with intertwined threads, the distraction screw may be introduced into bone more quickly and efficiently. Other advantages will be apparent from the foregoing description.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. A distractor system comprising:
   a distraction screw comprising a double threaded distal portion and a nonthreaded locking feature near a proximal end of the distraction screw;
   a crossbar;
   a first arm coupled to the crossbar;
   a second arm coupled to the crossbar and having an interior bore sized to receive at least a portion of the distraction screw;
   a key provided to engage a slot formed along the length in at least one of a distal arm portion of the first arm or the second arm, the key having a body portion configured to extend thorough at least one of the distal arm portions to engage a cap member and a button portion, the body portion having a nonthreaded aperture sized to receive at least a portion of the distraction screw therethrough and the button portion configured to engage a biasing member, the slot being configured to receive the key therein to engage the distraction screw, wherein the key is configurable in a first position and a second position, and when configured in the first position the key engages the locking feature to substantially inhibit axial movement of the distraction screw within the interior bore, and when configured in the second position the key substantially permits axial movement of the distraction screw within the interior bore;
   a biasing member provided between the button portion of the key and a first side of the distal arm portion; and, a cap member provided to engage an opposing second side of the distal arm portion and configured to attach to an end portion of the key to retain the key in the slot when inserted therein.

2. The distractor system of claim 1, wherein the key is biased into the first position.

3. The distractor system of claim 2, wherein biasing member is a spring that biases the key into the first position.

4. The distractor system of claim 1, wherein the slot extends to the interior bore; and the key is slideably received within the slot.

5. The distractor system of claim 1, wherein:
the nonthreaded locking feature comprises a groove that extends at least part way around the distraction screw; and
the nonthreaded aperture of the key comprises a ridge that extends at least part way around an interior surface of the aperture and is sized to fit within the groove of the distraction screw.

6. The distractor system of claim 1, wherein:
the distraction screw further comprises an enlarged portion that has a diameter that is greater than a diameter of the interior bore; and
the second arm further includes a counterbore at an end of the interior bore, the counterbore sized to receive the enlarged portion.

7. The distractor system of claim 1, wherein the first arm includes a proximal arm portion and a distal arm portion having a slot formed therein and hingedly attached to the proximal arm portion at a connection pin such that the distal arm portion may be pivoted between a generally planar position with respect to the proximal end to a generally perpendicular position with respect to the proximal end,
wherein the second arm has a first portion and a second portion, the second portion being capable of being rotated relative to the first portion; the second arm including a proximal arm portion and a distal arm portion, the distal arm portion having a slot formed therein, and hingedly attached to the proximal arm portion at a connection pin such that the distal arm portion may be pivoted between a generally planar parallel position with respect to the proximal end to a generally perpendicular position with respect to the proximal end.

8. A distractor system comprising:
a first arm including a distal arm portion having an interior bore sized to receive at least a portion of a distraction screw; a first arm coupled to a crossbar; a key having a body portion configured to extend through the distal arm portion and a button portion, the body portion having a nonthreaded aperture sized to receive at least a portion of the distraction screw therethrough, the button portion configured to engage a biasing member and, the key configured to be inserted into a slot formed in at least one of the first arm or a second arm configured to receive the key therein to engage the distraction screw, wherein the key is configurable in a first position and a second position, when configured in the first position the key substantially inhibits axial movement of the distraction screw within the interior bore, and when configured in the second position the key substantially permits axial movement of the distraction screw within the interior bore;
a biasing member provided between the key and the distal arm portion; and,
a cap member provided to engage an opposing second side of the distal arm portion and configured to receive an end portion of the key to retain the key in the slot when inserted therein.

9. The distractor system of claim 8, wherein the second arm comprises a proximal arm portion and a distal arm portion movable with respect to the proximal arm portion.

10. The distractor system of claim 8, wherein the key is biased into the first position.

11. The distractor system of claim 10, wherein the key engages a spring that biases the key into the first position.

12. The distractor system of claim 8, wherein the slot extends to the interior bore; and
the key is slidably received within the slot.

13. The distractor system of claim 8, wherein the nonthreaded aperture of the key comprises a ridge that extends at least part way around an interior surface of the aperture and is sized to fit within a groove of the distraction screw.

14. The distractor system of claim 8, wherein the first arm further includes a counterbore at an end of the interior bore, the counterbore having a diameter that is greater than a diameter of the interior bore.

* * * * *